(12) United States Patent
Laxer et al.

(10) Patent No.: US 8,809,537 B2
(45) Date of Patent: Aug. 19, 2014

(54) N-ETHYL-4-HYDROXYL-1-METHYL-5-(METHYL(2,3,4,5,6-PENTAHYDROXYHEXYL) AMINO)-2-OXO-N-PHENYL-1,2-DIHYDROQUINOLINE-3-CARBOXAMIDE

(71) Applicants: Avital Laxer, Tel-Aviv (IL); Konstantin Ulanenko, Netanya (IL)

(72) Inventors: Avital Laxer, Tel-Aviv (IL); Konstantin Ulanenko, Netanya (IL)

(73) Assignee: Teva Pharmaceutical Industries, Ltd., Petach-TIkva (IL)

( * ) Notice: Subject to any disclaimer, the term of this patent is extended or adjusted under 35 U.S.C. 154(b) by 0 days.

(21) Appl. No.: 13/888,709

(22) Filed: May 7, 2013

(65) Prior Publication Data
US 2013/0345256 A1 Dec. 26, 2013

Related U.S. Application Data

(60) Provisional application No. 61/644,054, filed on May 8, 2012.

(51) Int. Cl.
*A61K 31/47* (2006.01)
*C07D 215/00* (2006.01)

(52) U.S. Cl.
USPC .......................................... 546/155; 514/312

(58) Field of Classification Search
None
See application file for complete search history.

(56) References Cited

U.S. PATENT DOCUMENTS

| | | | |
|---|---|---|---|
| 4,547,511 A | 10/1985 | Eriksoo et al. |
| 4,782,155 A | 11/1988 | Nakagawa et al. |
| 5,139,878 A | 8/1992 | Kim et al. |
| 6,077,851 A | 6/2000 | Bjork et al. |
| 6,121,287 A | 9/2000 | Bjork et al. |
| 6,133,285 A | 10/2000 | Bjork et al. |
| 6,593,343 B2 | 7/2003 | Bjork et al. |
| 6,605,616 B1 | 8/2003 | Bjork et al. |
| 6,875,869 B2 | 4/2005 | Jansson |
| 7,514,068 B2 | 4/2009 | Tung et al. |
| 7,528,131 B2 | 5/2009 | Persichetti et al. |
| 7,560,557 B2 | 7/2009 | Jansson |
| 7,589,208 B2 | 9/2009 | Jansson et al. |
| 7,884,208 B2 | 2/2011 | Frenkel et al. |
| 7,989,473 B2 | 8/2011 | Patashnik et al. |
| 8,178,127 B2 | 5/2012 | Safadi et al. |
| 8,252,933 B2 | 8/2012 | Gant et al. |
| 8,314,124 B2 | 11/2012 | Jansson et al. |
| 8,383,645 B2 | 2/2013 | Patashnik |
| 2002/0173520 A1 | 11/2002 | Bjork et al. |
| 2005/0192315 A1 | 9/2005 | Jansson et al. |
| 2005/0215586 A1 | 9/2005 | Jansson et al. |
| 2010/0209506 A1 | 8/2010 | Eisenreich |
| 2010/0322900 A1 | 12/2010 | Tarcic et al. |
| 2011/0027219 A1 | 2/2011 | Tarcic et al. |
| 2011/0034508 A1 | 2/2011 | Hayardeny et al. |
| 2011/0112141 A1 | 5/2011 | Frenkel et al. |
| 2011/0118308 A1 | 5/2011 | Frenkel et al. |
| 2011/0217295 A1 | 9/2011 | Haviv et al. |
| 2011/0218179 A1 | 9/2011 | Haviv et al. |
| 2011/0218203 A1 | 9/2011 | Kaye et al. |
| 2011/0251235 A1 | 10/2011 | Patashnik et al. |
| 2012/0010238 A1 | 1/2012 | Piryatinsky |
| 2012/0010239 A1 | 1/2012 | Fristedt |
| 2012/0142730 A1 | 6/2012 | Tarcic et al. |
| 2012/0225124 A1 | 9/2012 | Safadi et al. |
| 2013/0028866 A1 | 1/2013 | Gilgun et al. |
| 2013/0029916 A1 | 1/2013 | Gilgun et al. |
| 2013/0096158 A1 | 4/2013 | Hallak et al. |

FOREIGN PATENT DOCUMENTS

| | | |
|---|---|---|
| EP | 1073639 | 11/2002 |
| EP | 1097139 | 12/2002 |
| EP | 1095021 | 9/2003 |
| EP | 1511732 | 12/2006 |
| EP | 1720531 | 4/2011 |
| WO | WO90/15052 | 12/1990 |
| WO | WO99/55678 | 11/1999 |
| WO | WO00/03991 | 1/2000 |
| WO | WO00/03992 | 1/2000 |
| WO | WO00/74654 | 12/2000 |
| WO | WO 03/106424 | 12/2003 |
| WO | WO2005/074899 | 8/2005 |

OTHER PUBLICATIONS

Polman, Neurology 2005 vol. 64, pp. 987-991 Abstract.*
Written Opinion of the International Searching Authority issued Jun. 20, 2010 in connection with PCT International Application No. PCT/US2008/013890, filed Dec. 19, 2008.
International Preliminary Report on Patentability issued Jun. 22, 2010 in connection with PCT International Application No. PCT/US2008/013890, filed Dec. 19, 2008.
PCT International Search Report issued Nov. 21, 2011 in connection with PCT Intenrational Application No. PCT/US2011/43383, filed Jul. 8, 2011.
Written Opinion of the International Searching Authority issued Nov. 21, 2011 in connection with PCT Intenrational Application No. PCT/US2011/43383, filed Jul. 8, 2011.
International Preliminary Report on Patentability issued Jan. 15, 2013 in connection with PCT international Application No. PCT/US2011/043383, filed Jul. 8, 2011.
PCT International Search Report issued Nov. 29, 2011 in connection with PCT Intenrational Application No. PCT/US2011/43391, filed Jul. 8, 2011.

(Continued)

*Primary Examiner* — Heidi Reese
(74) *Attorney, Agent, or Firm* — John P. White; Gary J. Gershik; Cooper & Dunham LLP

(57) ABSTRACT

The subject invention provides pharmaceutical compositions containing laquinimod or a pharmaceutically acceptable salt thereof, an isolated compound of N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof, compositions containing N-ethyl-4-hydroxyl-1-methyl-5-(methyl(2,3,4,5,6-pentahydroxyhexyl)amino)-2-oxo-N-phenyl-1,2-dihydroquinoline-3-carboxamide and methods of preparing the same.

36 Claims, 8 Drawing Sheets

(56) References Cited

OTHER PUBLICATIONS

Written Opinion of the International Searching Authority issued Nov. 29, 2011 in connection with PCT Intenrational Application No. PCT/US2011/43391, filed Jul. 8, 2011.
International Preliminary Report on Patentability issued Jan. 15, 2013 in connection with PCT International Application No. PCT/US2011/043391, filed Jul. 8, 2011.
PCT International Search Report issued Apr. 24, 2013 in connection with PCT International Application No. PCT/US2013/26476, filed Feb. 15, 2013.
Written Opinion of the International Searching Authority issued Apr. 24, 2013 in connection with PCT International Application No. PCT/US2013/26476, filed Feb. 15, 2013.
Apr. 26, 2011 Office Action issued by the U.S. Patent and Trademark Office in connection with U.S. Appl. No. 12/317,104.
May 12, 2011 Response to Apr. 26, 2011 Office Action filed in connection with U.S. Appl. No. 12/317,104.
Jun. 29, 2011 Office Action issued by the U.S. Patent and Trademark Office in connection with U.S. Appl. No. 12/317,104.
Sep. 29, 2011 Response to Jun. 29, 2011 Office Action filed in connection with U.S. Appl. No. 12/317,104.
Sep. 10, 2012 Office Action issued by the U.S. Patent and Trademark Office in connection with U.S. Appl. No. 13/178,842 680.
Dec. 10, 2012 Response to Sep. 10, 2012 Office Action filed in connection with U.S. Appl. No. 13/178,842.
Oct. 31, 2012 Office Action issued by the U.S. Patent and Trademark Office in connection with U.S. Appl. No. 13/471,175.
Nov. 30, 2012 Response to Oct. 31, 2012 Office Action filed in connection with U.S. Appl. No. 13/471,175.
Feb. 4, 2013 Office Action issued by the U.S. Patent and Trademark Office in connection with U.S. Appl. No. 13/471,175.
May 6, 2013 Response to Oct. 31, 2012 Office Action filed in connection with U.S. Appl. No. 13/471,151.
Feb. 13, 2013 Office Action issued by the U.S. Patent and Trademark Office in connection with U.S. Appl. No. 13/178,842.
Mar. 25, 2013 Office Action issued by the U.S. Patent and Trademark Office in connection with U.S. Appl. No. 13/178,865.
Apr. 25 Response to Mar. 25, 2013 Office Action filed in connection with U.S. Appl. No. 13/178,865.
Jul. 9, 2013 Office Action issued by the U.S. Patent and Trademark Office in connection with U.S. Appl. No. 13/178,865.
Jan. 17, 2011 European Search Opinion issued in connection with European Patent Application No. 08864658.3, filed Dec. 19, 2008.
Jun. 25, 2012 Official Communication issued in connection with European Patent Application No. 08864658.3, filed Dec. 19, 2008.
Oct. 26, 2012 Response to Jun. 25, 2012 Official Communication filed in connection with European Patent Application No. 08864658.3, filed Dec. 19, 2008.
Tuvesson et al. (2005) "Cytochrome P450 3A4 is the Major Enzyme Responsible for the Metabolism of Laquinimod, . . . " Drug Metabolism and Disposition 33(6):866-872.
Wennerberg et al. (2007) "Development of a Practical and Reliable Synthesis of Laquinimod", Organic Process Research & Development 111:674-680.

* cited by examiner

N-ETHYL-4-HYDROXYL-1-METHYL-5-(METHYL(2,3,4,5,6-PENTAHYDROXYHEXYL) AMINO)-2-OXO-N-PHENYL-1,2-DIHYDROQUINOLINE-3-CARBOXAMIDE

This application claims benefit of U.S. Provisional Application No. 61/644,054, filed May 8, 2012, the entire content of which is hereby incorporated by reference herein.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2-dihydro-4-hydroxy-5-chloro-1-methyl-2-oxoquinoline-3-carboxamide, and its Chemical Registry number is 248281-84-7. The processes of synthesis of laquinimod and the preparation of its sodium salt are disclosed in U.S. Pat. No. 6,077,851. An additional process of synthesis of laquinimod is disclosed in U.S. Pat. No. 6,875,869. Pharmaceutical compositions comprising laquinimod sodium are disclosed in PCT International Application Publication No. WO 2005/074899.

Laquinimod sodium has high oral bioavailability and has been suggested as an oral formulation for the treatment of Multiple Sclerosis (MS). (Polman, C. et al., (2005) "Treatment with laquinimod reduces development of active MRI lesions in relapsing MS", Neurology. 64:987-991; Sandberg-Wollheim M, et al. (2005) "48-week open safety study with high-dose oral laquinimod in patients", *Mult Scler.* 11:S154). Studies have also shown that laquinimod can reduce development of active MRI lesions in relapsing MS. (Polman, C. et al., (2005) "Treatment with laquinimod reduces development of active MRI lesions in relapsing MS", Neurology. 64:987-991).

SUMMARY OF THE INVENTION

The subject invention provides an isolated compound having the structure:

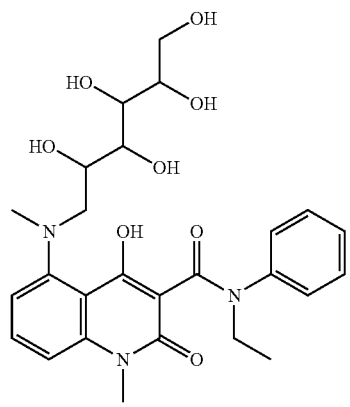 [SMILES: CCN(C(=O)c1c(O)c2c(N(C)CC(O)C(O)C(O)C(O)CO)cccc2n(C)c1=O)c1ccccc1]

or a salt thereof.

The subject invention also provides a composition comprising a compound having the structure:

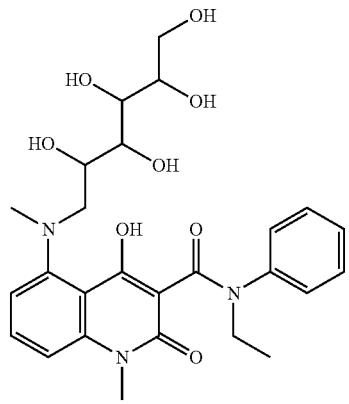 [SMILES: CCN(C(=O)c1c(O)c2c(N(C)CC(O)C(O)C(O)C(O)CO)cccc2n(C)c1=O)c1ccccc1]

or a salt thereof,
wherein the composition is free of laquinimod or a salt thereof.

The subject invention also provides a process for preparing N-ethyl-4-hydroxyl-1-methyl-5-(methyl(2,3,4,5,6-pentahydroxyhexyl)amino)-2-oxo-N-phenyl-1,2-dihydroquinoline-3-carboxamide comprising the steps of: a) reacting laquinimod or a salt thereof with meglumine in an aqueous solution; b) adjusting the pH of the aqueous solution to less than 2; and c) isolating and obtaining N-ethyl-4-hydroxyl-1-methyl-5-(methyl(2,3,4,5,6-pentahydroxyhexyl)amino)-2-oxo-N-phenyl-1,2-dihydroquinoline-3-carboxamide from the reaction mixture.

The subject invention also provides a process for preparing N-ethyl-4-hydroxyl-1-methyl-5-(methyl(2,3,4,5,6-pentahydroxyhexyl)amino)-2-oxo-N-phenyl-1,2-dihydroquinoline-3-carboxamide comprising the steps of: a) dissolving 5-iodo-laquinimod, meglumine and CuI in Dimethylformamide (DMF) to form a mixture; b) removing DMF from the mixture of step a) to obtain an residue; c) dissolving the residue from step b) in methanol to obtain a mixture; d) adding silica gel to the mixture of step c) to obtain a suspension; e) evaporating the suspension of step d) to dryness; and f) isolating and obtaining N-ethyl-4-hydroxyl-1-methyl-5-(methyl(2,3,4,5,6-pentahydroxyhexyl)amino)-2-oxo-N-phenyl-1,2-dihydroquinoline-3-carboxamide from the suspension of step e).

The subject invention also provides N-ethyl-4-hydroxyl-1-methyl-5-(methyl(2,3,4,5,6-pentahydroxyhexyl)amino)-2-oxo-N-phenyl-1,2-dihydroquinoline-3-carboxamide prepared the methods disclosed herein.

The subject invention also provides a pharmaceutical composition comprising laquinimod or a pharmaceutically acceptable salt thereof, N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof, and at least one pharmaceutically acceptable carrier, wherein N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount greater than about 0.1% w/w, relative to the amount of laquinimod, based on a determination by an HPLC method.

The subject invention also provides a process for preparing a validated pharmaceutical composition comprising laquinimod or a pharmaceutically acceptable salt thereof, and at least one pharmaceutically acceptable carrier, comprising: a) obtaining a batch of laquinimod or a pharmaceutically acceptable salt thereof; b) determining the amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the batch using a suitable apparatus; and c) preparing the pharmaceutical composition from the batch only if the batch is determined to have not more than about 1.0% N-ethyl-4-hydroxyl-1-methyl-5-(methyl(2,3,4,5,6-pentahydroxyhexyl)amino)-2-oxo-N-phenyl-1,2-dihydroquinoline-3-carboxamide by weight relative to the amount of laquinimod.

The subject invention also provides a process for preparing a packaged pharmaceutical composition comprising laquinimod or a pharmaceutically acceptable salt thereof comprising: a) obtaining a pharmaceutical composition of laquinimod or a pharmaceutically acceptable salt thereof; b) analyzing the pharmaceutical composition for the presence of N-ethyl-4-hydroxyl-1-methyl-5-(methyl(2,3,4,5,6-pentahydroxyhexyl)amino)-2-oxo-N-phenyl-1,2-dihydroquinoline-3-carboxamide; and c) packaging the pharmaceutical composition in a light-resistant packaging only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide is not more than about 1.0% by weight relative to the amount of laquinimod.

The subject invention also provides a process of distributing a validated batch of a pharmaceutical composition comprising laquinimod or a pharmaceutically acceptable salt thereof and at least one pharmaceutically acceptable carrier, comprising: a) obtaining a batch of the pharmaceutical composition; b) performing stability testing with a sample of the batch; c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample of the batch by a suitable apparatus after stability testing; d) validating the batch for distribution only if the sample of the batch after stability testing is determined to have not more than about 1.0% by weight of N-ethyl-4-hydroxyl-1-methyl-5-(methyl(2,3,4,5,6-pentahydroxyhexyl)amino)-2-oxo-N-phenyl-1,2-dihydroquinoline-3-carboxamide relative to the amount of laquinimod; and e) distributing the validated batch.

The subject invention also provides N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof for use as a reference standard to detect trace amounts of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in a pharmaceutical composition comprising laquinimod or a pharmaceutically acceptable salt of laquinimod.

The subject invention also provides a method for treating a patient afflicted with Multiple Sclerosis comprising administering to the patient an amount of the pharmaceutical composition described herein effective to treat Multiple Sclerosis in the patient.

The subject invention also provides an isolated compound having the structure:

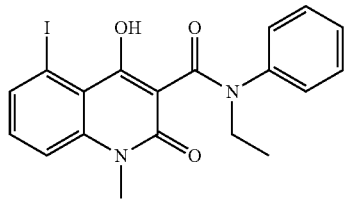 [SMILES: CCN(C(=O)c1c(O)c2c(I)cccc2n(C)c1=O)c1ccccc1]

or a salt thereof.

The subject invention also provides a process for preparing a pharmaceutical composition comprising laquinimod or a pharmaceutically acceptable salt thereof comprising: a) a) obtaining a batch of laquinimod or a pharmaceutically acceptable salt thereof; b) performing stability testing with a sample from the batch; c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample by a suitable apparatus after stability testing; and d) preparing the pharmaceutical composition from the batch only if the batch is determined to have not more than about 1.0% N-ethyl-4-hydroxyl-1-methyl-5-(methyl(2,3,4,5,6-pentahydroxyhexyl)amino)-2-oxo-N-phenyl-1,2-dihydroquinoline-3-carboxamide by weight relative to the amount of laquinimod.

The subject invention also provides a process for preparing a packaged pharmaceutical composition comprising laquinimod or a pharmaceutically acceptable salt thereof comprising: a) obtaining a batch of pharmaceutical composition comprising laquinimod or a pharmaceutically acceptable salt thereof; b) performing stability testing with a sample from the batch; c) determining the total amount of N-ethyl-4-hydroxyl-1-methyl-5-(methyl(2,3,4,5,6-pentahydroxyhexyl) amino)-2-oxo-N-phenyl-1,2-dihydroquinoline-3-carboxamide in the sample by a suitable apparatus after stability testing; and d) packaging the pharmaceutical composition in only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample is determined to be not more than about 1.0% by weight relative to the amount of laquinimod.

DETAILED DESCRIPTION OF THE INVENTION

Figure 1:
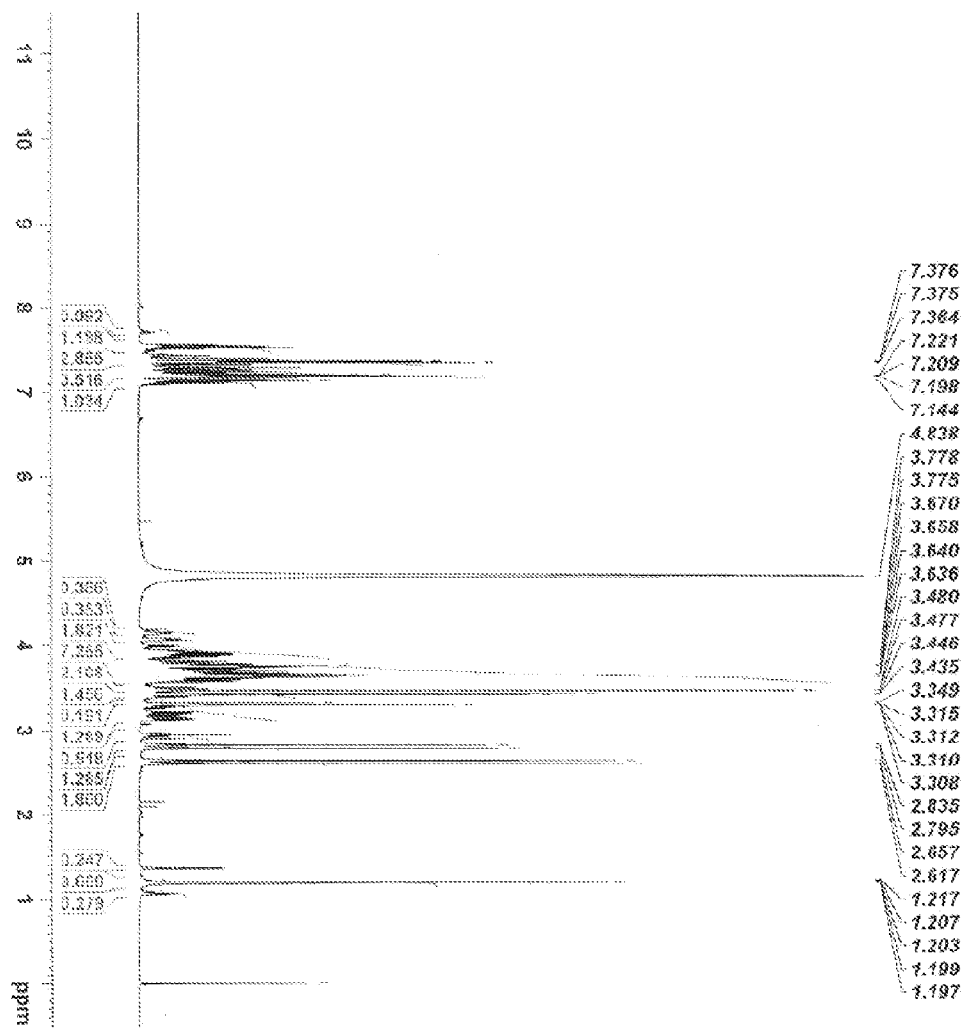
FIG. 1. $^1$H-NMR spectrum of MEG-LAQ in $CD_3OD$—0.6 ppm/cm according to Example 1A.
Figure 2:
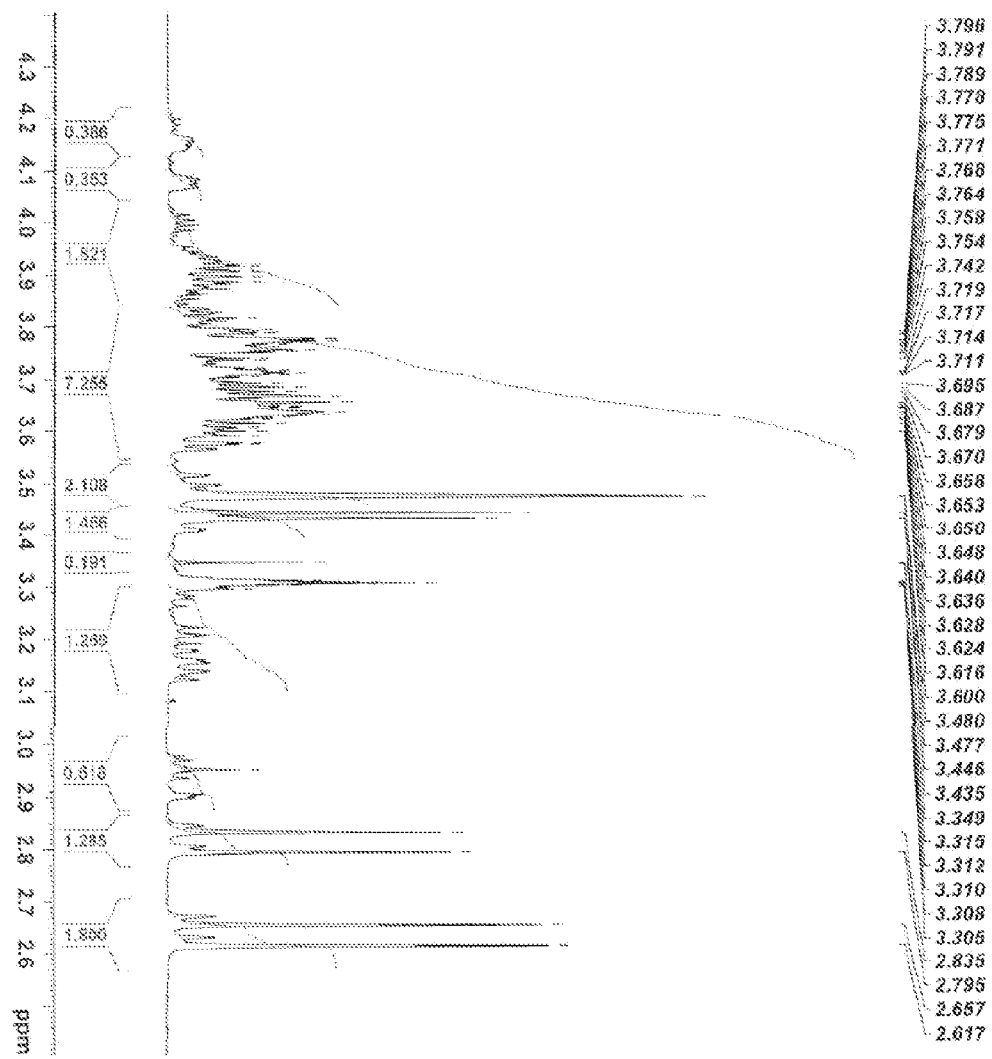
FIG. 2. $^1$H-NMR spectrum of MEG-LAQ in $CD_3OD$—0.0994 ppm/cm according to Example 1A.
Figure 3:
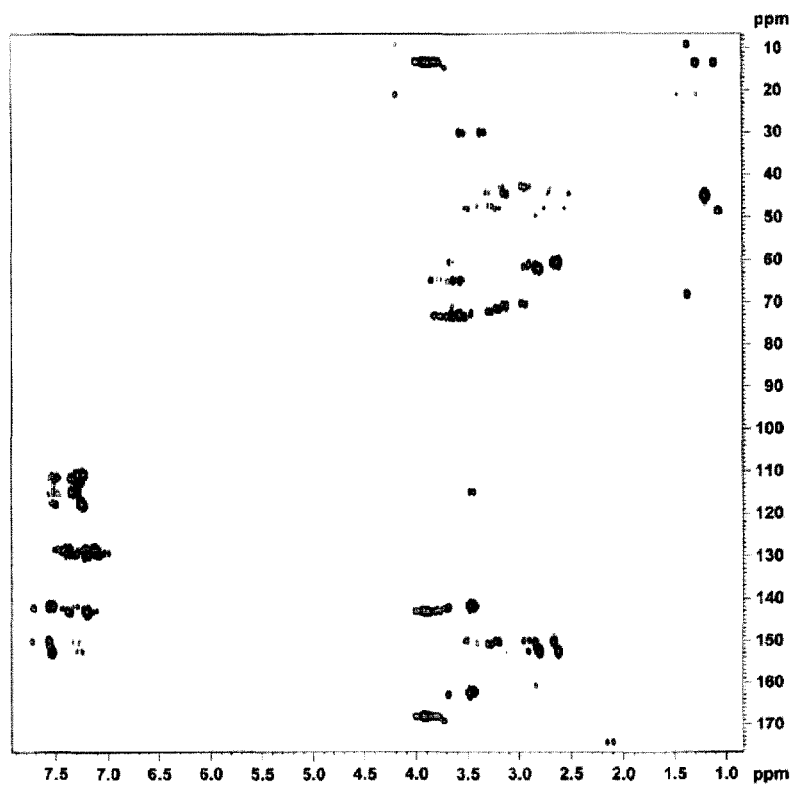
FIG. 3. 2D-NMR (HMBC) of MEG-LAQ in $CD_3OD$ according to Example 1A.
Figure 4:
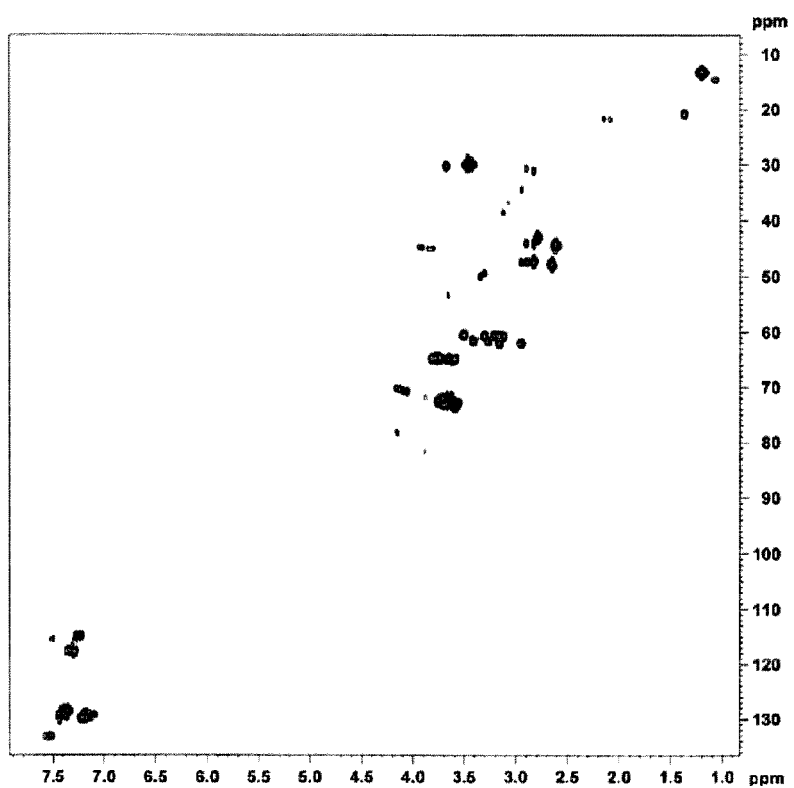
FIG. 4. 2D-NMR (HMQC) of MEG-LAQ in $CD_3OD$ according to Example 1A.
Figure 5:
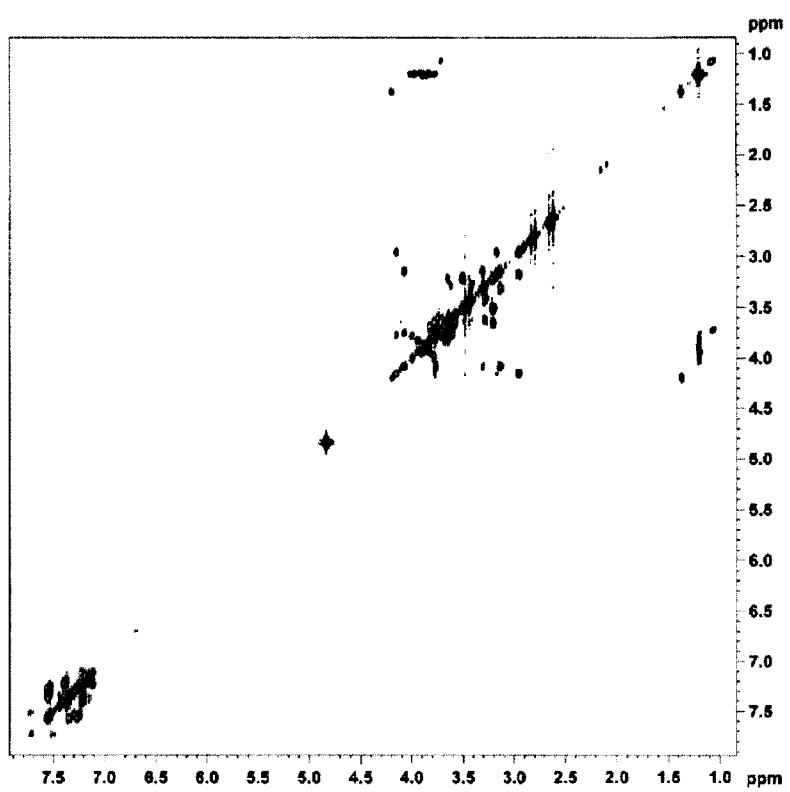
FIG. 5. 2D-NMR (COSY) of MEG-LAQ in $CD_3OD$ according to Example 1A.
Figure 6:
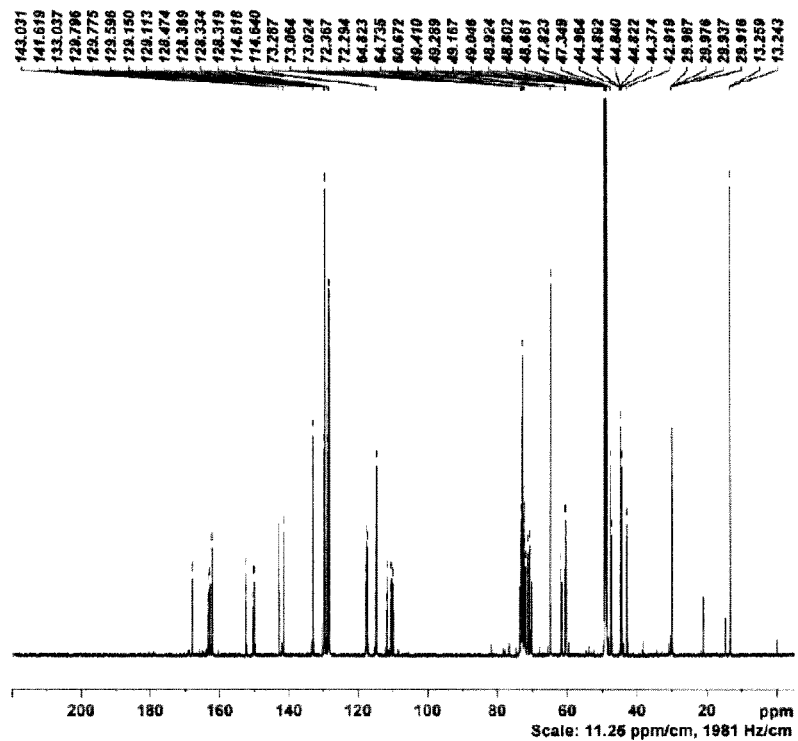
FIG. 6. $^{13}$C-NMR spectrum of MEG-LAQ in $CD_3OD$ according to Example 1A.

Laquinimod is a small molecule having the following chemical structure:

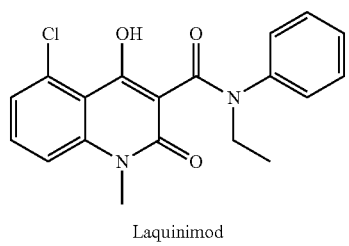 [SMILES: CCN(C(=O)c1c(O)c2c(Cl)cccc2n(C)c1=O)c1ccccc1]

Laquinimod

It is an oral immunomodulator which has demonstrated therapeutic effect in various experimental inflammatory/autoimmune animal models, such as Experimental Autoimmune Encephalomyelitis (EAE), an animal model for Multiple Sclerosis (MS), Dextran Sodium Sulphate (DSS) induced colitis for Inflammatory Bowel Disease, Non-Obese Diabetic (NOD) mice for Type I Diabetes (IDDM), Experimental Autoimmune Neuritis (EAN) for Guillain-Barre Syndrome, Systemic Lupus Erythematosus (SLE), lupus nephritis, lupus arthritis, Crohn's Disease and Rheumatoid arthritis. The therapeutic activity of laquinimod in these models results from a variety of mechanistic effects, including reduction of leukocyte infiltration into target tissues by modulation of chemokine-mediated T-cell adhesion, modulation of cytokine balance, down regulation of MHC class II resulting in alteration of antigen presentation, and effects on dendritic cells subpopulations.

It has been found that when a pharmaceutical composition containing laquinimod or salts thereof and N-methylglucamine (meglumine) is exposed to extreme conditions, an impurity is formed. This impurity was identified to be N-ethyl-4-hydroxyl-1-methyl-5-(methyl(2,3,4,5,6-pentahydroxyhexyl)amino)-2-oxo-N-phenyl-1,2-dihydroquinoline-3-carboxamide ("MEG-LAQ"), having the following structure:

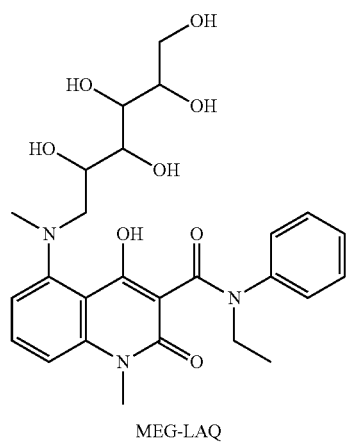 [SMILES: CCN(C(=O)c1c(O)c2c(N(C)CC(O)C(O)C(O)C(O)CO)cccc2n(C)c1=O)c1ccccc1]

MEG-LAQ

Not to be bound by a particular theory, this impurity is suspected to be formed via a substitution reaction in which the chlorine group of laquinimod is substituted as shown in the above MEG-LAQ structure.

The subject invention provides an isolated compound having the structure:

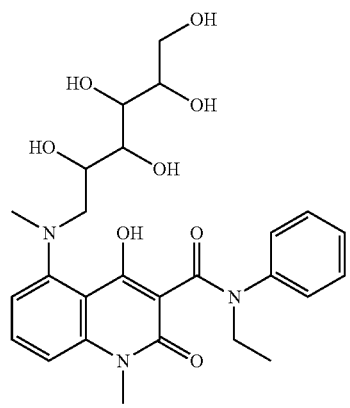 [SMILES: CCN(C(=O)c1c(O)c2c(N(C)CC(O)C(O)C(O)C(O)CO)cccc2n(C)c1=O)c1ccccc1]

or a salt thereof. In an embodiment, the isolated compound is in mono-hydrate form.

The subject invention also provides a composition comprising a compound having the structure:

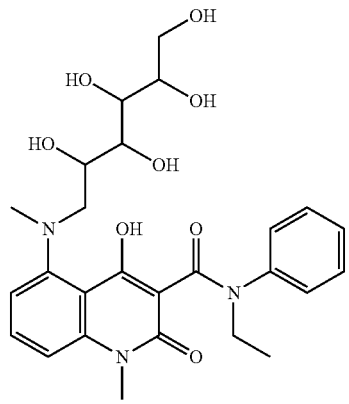 [SMILES: CCN(C(=O)c1c(O)c2c(N(C)CC(O)C(O)C(O)C(O)CO)cccc2n(C)c1=O)c1ccccc1]

or a salt thereof,
wherein the composition is free of laquinimod or a salt thereof. In an embodiment, the compound is in mono-hydrate form.

The subject invention also provides a process for preparing N-ethyl-4-hydroxyl-1-methyl-5-(methyl(2,3,4,5,6-pentahydroxyhexyl)amino)-2-oxo-N-phenyl-1,2-dihydroquinoline-3-carboxamide comprising the steps of: a) reacting laquinimod or a salt thereof with meglumine in an aqueous solution; b) adjusting the pH of the aqueous solution to less than 2; and c) isolating and obtaining N-ethyl-4-hydroxyl-1-methyl-5-(methyl(2,3,4,5,6-pentahydroxyhexyl)amino)-2-oxo-N-phenyl-1,2-dihydroquinoline-3-carboxamide from the reaction mixture. In one embodiment, the laquinimod is a salt of laquinimod. In another embodiment, the salt of laquinimod is a sodium salt.

The subject invention also provides a process for preparing N-ethyl-4-hydroxyl-1-methyl-5-(methyl(2,3,4,5,6-pentahydroxyhexyl)amino)-2-oxo-N-phenyl-1,2-dihydroquinoline-3-carboxamide comprising the steps of: a) dissolving 5-iodo-laquinimod, meglumine and CuI in Dimethylformamide (DMF) to form a mixture; b) removing DMF from the mixture of step a) to obtain an residue; c) dissolving the residue from step b) in methanol to obtain a mixture; d) adding silica gel to the mixture of step c) to obtain a suspension; e) evaporating the suspension of step d) to dryness; and f) isolating and obtaining N-ethyl-4-hydroxyl-1-methyl-5-(methyl(2,3,4,5,6-pentahydroxyhexyl)amino)-2-oxo-N-phenyl-1,2-dihydroquinoline-3-carboxamide from the suspension of step e).

In one embodiment, the mixture of step a) is stirred for 2 hours at 35-38° C. prior to step b). In another embodiment, step b) is achieved by DMF distillation at 2 mbar vacuum. In another embodiment, step f) is achieved by flash column chromatography on silica gel.

The subject invention also provides N-ethyl-4-hydroxyl-1-methyl-5-(methyl(2,3,4,5,6-pentahydroxyhexyl)amino)-2-oxo-N-phenyl-1,2-dihydroquinoline-3-carboxamide prepared the methods disclosed herein.

The subject invention also provides a pharmaceutical composition comprising laquinimod or a pharmaceutically acceptable salt thereof, N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof, and at least one pharmaceutically acceptable carrier, wherein N-ethyl-4-hydroxyl-1-methyl-5-(methyl(2,3,4,5,6-pentahydroxyhexyl)amino)-2-oxo-N-phenyl-1,2-dihydroquinoline- 3-carboxamide is present in the pharmaceutical composition in an amount greater than about 0.1% w/w, relative to the amount of laquinimod, based on a determination by an HPLC method.

In an embodiment of the present invention, N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount greater than about 0.2% w/w, relative to the amount of laquinimod, based on a determination by an HPLC method. In another embodiment, N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount not more than about 1.0%, by weight, relative to the amount of laquinimod, based on a determination by an HPLC method.

In one embodiment, the pharmaceutical composition is less than one week old, and the temperature during the less than one week did not exceed ambient temperature. In another embodiment, the at least one pharmaceutically acceptable carrier is magnesium stearate.

In an embodiment, the pharmaceutical composition comprises a pharmaceutically acceptable salt of laquinimod. In another embodiment, the pharmaceutically acceptable salt of laquinimod is a sodium salt. In another embodiment, the pharmaceutical composition is in the form of a capsule. In another embodiment, the pharmaceutical composition is in the form of a tablet.

The subject invention also provides a process for preparing a validated pharmaceutical composition comprising laquinimod or a pharmaceutically acceptable salt thereof, and at least one pharmaceutically acceptable carrier, comprising: a) obtaining a batch of laquinimod or a pharmaceutically acceptable salt thereof; b) determining the amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the batch using a suitable apparatus; and c) preparing the pharmaceutical composition from the batch only if the batch is determined to have not more than about 1.0% N-ethyl-4-hydroxyl-1-methyl-5-(methyl(2,3,4,5,6-pentahydroxyhexyl)amino)-2-oxo-N-phenyl-1,2-dihydroquinoline-3-carboxamide by weight relative to the amount of laquinimod.

The subject invention also provides a process for preparing a packaged pharmaceutical composition comprising laquinimod or a pharmaceutically acceptable salt thereof comprising: a) obtaining a pharmaceutical composition of laquinimod or a pharmaceutically acceptable salt thereof; b) analyzing the pharmaceutical composition for the presence of N-ethyl-4-hydroxyl-1-methyl-5-(methyl(2,3,4,5,6-pentahydroxyhexyl)amino)-2-oxo-N-phenyl-1,2-dihydroquinoline-3-carboxamide; and c) packaging the pharmaceutical composition in a light-resistant packaging only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide is not more than about 1.0% by weight relative to the amount of laquinimod.

The subject invention also provides a process of distributing a validated batch of a pharmaceutical composition comprising laquinimod or a pharmaceutically acceptable salt thereof and at least one pharmaceutically acceptable carrier, comprising: a) obtaining a batch of the pharmaceutical composition; b) performing stability testing with a sample of the batch; c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample of the batch by a suitable apparatus after stability testing; d) validating the batch for distribution only if the sample of the batch after stability testing is determined to have not more than about 1.0% by weight of N-ethyl-4-hydroxyl-1-methyl-5-(methyl(2,3,4,5,6-pentahydroxyhexyl)amino)-2-oxo-N-phenyl-1,2-dihydroquinoline-3-carboxamide relative to the amount of laquinimod; and e) distributing the validated batch.

In one embodiment, the pharmaceutical composition comprises the pharmaceutically acceptable salt of laquinimod which is a sodium salt.

The subject invention also provides N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof for use, as a reference standard to detect trace amounts of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in a pharmaceutical composition comprising laquinimod or a pharmaceutically acceptable salt of laquinimod.

The subject invention also provides a method for treating a patient afflicted with Multiple Sclerosis comprising administering to the patient an amount of the pharmaceutical composition described herein effective to treat Multiple Sclerosis in the patient.

The subject invention also provides an isolated compound having the structure:

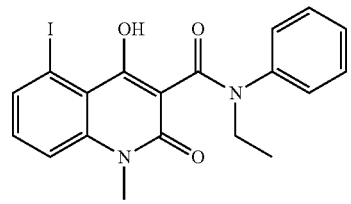 [SMILES: CCN(C(=O)c1c(O)c2c(I)cccc2n(C)c1=O)c1ccccc1]

or a salt thereof.

The subject invention also provides a process for preparing a pharmaceutical composition comprising laquinimod or a pharmaceutically acceptable salt thereof comprising: a) a) obtaining a batch of laquinimod or a pharmaceutically acceptable salt thereof; b) performing stability testing with a sample from the batch; c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample by a suitable apparatus after stability testing; and d) preparing the pharmaceutical composition from the batch only if the batch is determined to have not more than about 1.0% N-ethyl-4-hydroxyl-1-methyl-5-(methyl(2,3,4,5,6-pentahydroxyhexyl)amino)-2-oxo-N-phenyl-1,2-dihydroquinoline-3-carboxamide by weight relative to the amount of laquinimod.

The subject invention also provides a process for preparing a packaged pharmaceutical composition comprising laquinimod or a pharmaceutically acceptable salt thereof comprising: a) obtaining a batch of pharmaceutical composition comprising laquinimod or a pharmaceutically acceptable salt thereof; b) performing stability testing with a sample from the batch; c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample by a suitable apparatus after stability testing; and d) packaging the pharmaceutical composition in only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample is determined to be not more than about 1.0% by weight relative to the amount of laquinimod.

Every embodiment disclosed herein can be combined with every other embodiment of the subject invention, unless specified otherwise.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^{1}H$, $^{2}H$, or $^{3}H$. Furthermore, any compounds containing $^{2}H$ or $^{3}H$ may specifically have the structure of any of the compounds disclosed herein.

Isotopically-labeled compounds can generally be prepared by conventional techniques known to those skilled in the art or by processes analogous to those described in the Examples disclosed herein using an appropriate isotopically-labeled reagents in place of the non-labeled reagents employed.

A characteristic of a compound refers to any quality that a compound exhibits, e.g., peaks or retention times, as determined by 1H nuclear magnetic spectroscopy, mass spectroscopy, infrared, ultraviolet or fluorescence spectrophotometry, gas chromatography, thin layer chromatography, high performance liquid chromatography (HPLC), elemental analysis, Ames test, dissolution, stability and any other quality that can be determined by an analytical method. Once the characteristics of a compound are known, the information can be used to, for example, screen or test for the presence of the compound in a sample. Quantity or weight percentage of a compound present in a sample can be determined by a suitable apparatus, for example, a HPLC.

A "detection limit" for an analytical method used in screening or testing for the presence of a compound in a sample is a threshold under which the compound in a sample cannot be detected by the analytical method used. For example, the detection limit of a HPLC method for MEG-LAQ in a sample containing laquinimod is 0.1% by weight relative to the amount of laquinimod.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

As used herein, an "isolated" compound is a compound isolated from the crude reaction mixture following an affirmative act of isolation. The act of isolation necessarily involves separating the compound from the other known components of the crude reaction mixture, with some impurities, unknown side products and residual amounts of the other known components of the crude reaction mixture permitted to remain. Purification is an example of an affirmative act of isolation.

As used herein, a composition that is "free" of a chemical entity means that the composition contains, if at all, an amount of the chemical entity which cannot be avoided following an affirmative act intended to purify the composition by separating the chemical entity from the composition. A composition which is "free" of a laquinimod of a salt thereof, if present, as used herein, means that the laquinimod or a salt thereof is a minority component relative to the amount of MEG-LAQ, by weight.

As used herein, "stability testing" refers to tests conducted at specific time intervals and various environmental conditions (e.g., temperature and humidity) to see if and to what extent a drug product degrades over its designated shelf life time. The specific conditions and time of the tests are such that they accelerate the conditions the drug product is expected to encounter over its shelf life. For example, detailed requirements of stability testing for finished pharmaceuticals are codified in C.F.R §211.166, the entire content of which is hereby incorporated by reference.

As used herein, a pharmaceutical composition which is "X weeks old" refers to the period of time, in this case one week, since the pharmaceutical composition was made.

As used herein, "ambient temperature" refers a temperature of from about 20° C. to about 30° C.

As used herein, "about" in the context of a measurable numerical value means the numerical value within the standard error of the analytical method used to measure.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat multiple sclerosis. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, to "treat" or "treating" encompasses, e.g., inducing inhibition, regression, or stasis of, or alleviating a symptom of, a disorder and/or disease. As used herein, "inhibition" of disease progression or disease complication in a subject means preventing or reducing the disease progression and/or disease complication. "Ameliorating" or "alleviating" a condition or state as used herein shall mean to relieve or lessen the symptoms of that condition or state.

A dosage unit may comprise a single compound or mixtures of compounds thereof. A dosage unit can be prepared for oral dosage forms, such as tablets, capsules, pills, powders, and granules.

A pharmaceutically acceptable salt of laquinimod includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, which are hereby incorporated by reference into this application.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Specific examples of the techniques, pharmaceutically acceptable carriers and excipients that may be used to formulate oral dosage forms of the present invention are described, e.g., in U.S. Pat. No. 7,589,208, PCT International Application Publication Nos. WO 2005/074899, WO 2007/047863, and 2007/146248.

General techniques and compositions for making dosage forms useful in the present invention are described-in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol. 40 (Gilbert S. Banker, Christopher T. Rhodes, Eds.). These references in their entireties are hereby incorporated by reference into this application.

This invention will be better understood by reference to the Experimental Details which follow, but those skilled in the art will readily appreciate that the specific experiments detailed are only illustrative of the invention as described more fully in the claims which follow thereafter.

Experimental Details

Example 1A

Formation of MEG-LAQ

Amount of MEG-LAQ sufficient for characterization of its chemical structure was obtained by bubbling air through an aqueous solution of laquinimod sodium and meglumine under reflux conditions for about 1 month. The obtained solution was diluted twice with water and acidified with concentrated hydrochloric acid to pH 1-2. The aqueous solution was filtered followed by extraction with chloroform. Then, a concentrated ammonium hydroxide solution was added to the aqueous solution, up to neutralization. The solution was evaporated and the obtained brown syrup was washed with methanol. Meglumine was solidified and filtered followed by silica gel addition to the methanolic solution. The solvent was evaporated and the obtained mixture was purified by silica-gel column chromatography (mobile phase: 20% methanol in dichloromethane). A sample of the resulting compound was characterized by NMR, MS, elemental analysis and FT-IR, which demonstrated the compound to correspond with the molecular structure below:

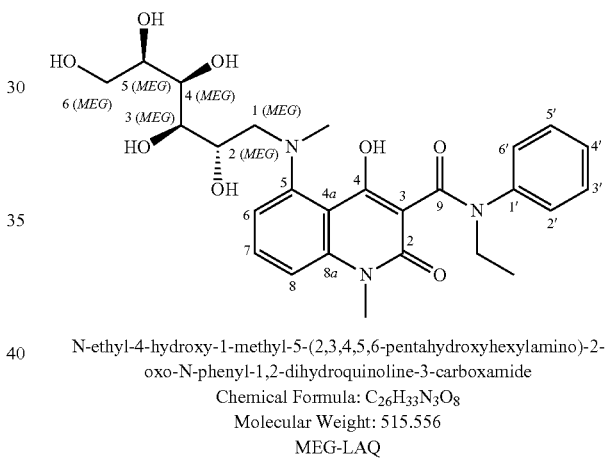

N-ethyl-4-hydroxy-1-methyl-5-(2,3,4,5,6-pentahydroxyhexylamino)-2-oxo-N-phenyl-1,2-dihydroquinoline-3-carboxamide
Chemical Formula: $C_{26}H_{33}N_3O_8$
Molecular Weight: 515.556
MEG-LAQ Elemental Analysis The test for elemental analysis was performed on a Perkin-Elmer 2400 Series II C H N Analyzer. The results for MEG-LAQ are presented in Table 1 below. Based on the elemental analysis results, there is high agreement that the MEG-LAQ is in the mono-hydrate form.

TABLE 1

Element Analysis Results for MEG-LAQ

| Element | % C | % H | % N |
|---|---|---|---|
| Theoretical | 60.57 | 6.45 | 8.15 |
| Theoretical Hydrate | 58.53 | 6.61 | 7.88 |
| Experimental | 58.57 | 6.57 | 7.72 |

NMR Spectroscopy

The $^1$H-NMR and $^{13}$C-NMR characterization of MEG-LAQ was performed in $CD_3OD$ on a Bruker Avance III—700NMR spectrometer and included regular experiments as well as three 2D experiments. The spectra are shown in FIGS. 1-6.

The assignments of the protons and carbons are very complex. It is useful to focus on the region of 2.6-2.9 ppm in the $^1$H-NMR spectra: Four large singlets can be seen, which correspond to the N-methyl group of the amine of the sugar moiety. The corresponding carbons appear in the 42-48 ppm region. The reason for the four peaks is most probably the existence of four conformers in solution: First, the two possible amide rotamers (see the NMR results of laquinimod sodium drug substance) and then each of the rotamers gives a pair of sets of signals because the N-phenyl-N-ethyl amide moiety is out of the plane of the heterocyclic ring, creating biphenyl type chirality. When this chiral element is connected to the optically active sugar, two possibly inter-converting diastereomers are formed. In the same region four additional minor similar signals can be seen, possibly originating from partial sugar epimerization during the reaction.

Mass Spectrometry

The mass spectrum of MEG-LAQ was obtained on a Q-TOF Micro-TM-MICROMASS (TOF) mass spectrometer, using electrospray ionization in positive ion mode (ES$^+$).

Figure 7:
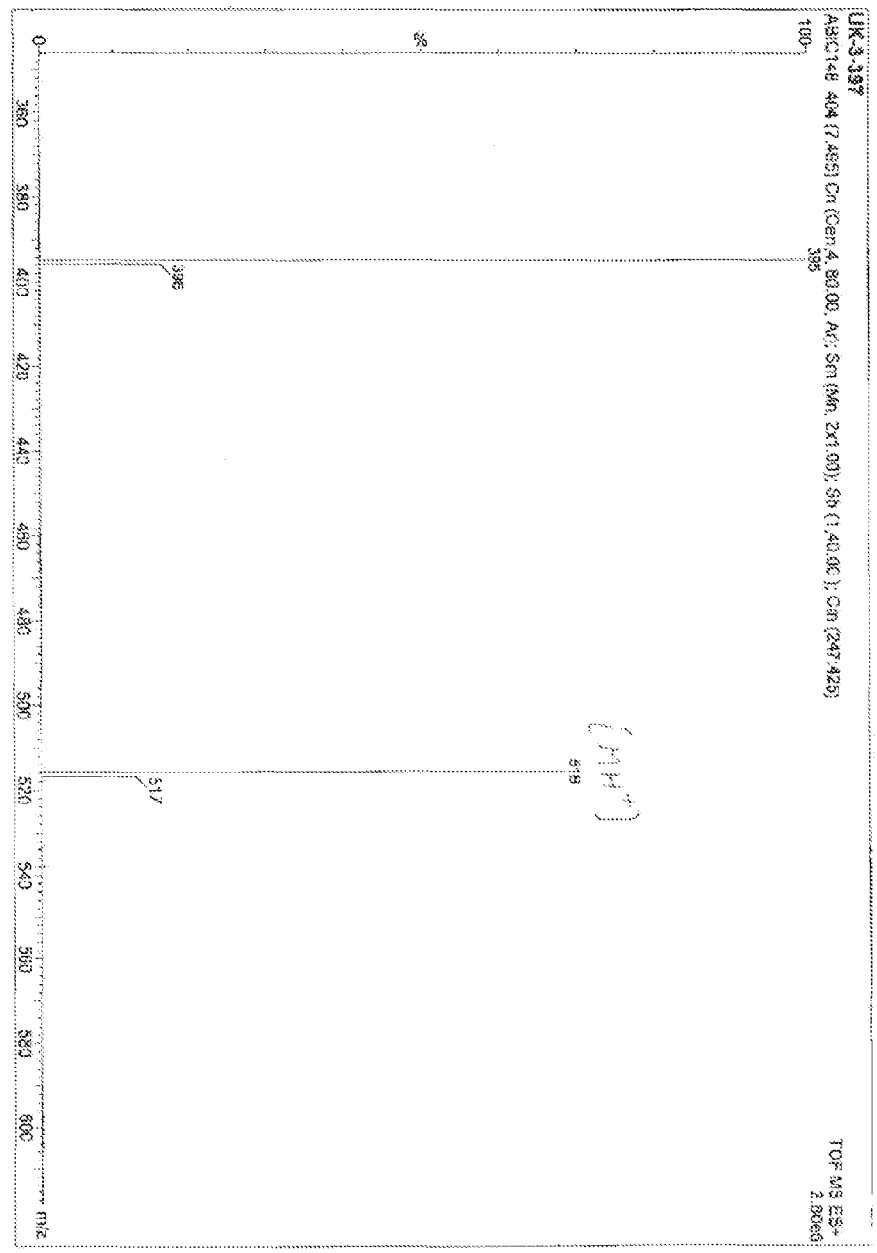
FIG. 7. Mass Spectrum of MEG-LAQ (ES$^+$ mode) according to Example 1A.

The mass spectrum is shown in FIG. 7 and is in agreement with the calculated molecular weight of MEG-LAQ.

The attribution of the main signals in ES$^+$ mass spectrum of MEG-LAQ is presented in Table 2.

TABLE 2

Attribution of main peaks of ES$^+$ mass spectrum of MEG-LAQ

| m/z | Attribution |
| --- | --- |
| 395 | [M-(N-Ethylaniline)]$^+$ |
| 516 | [M + H]$^+$ |

FT-IR

Figure 8:
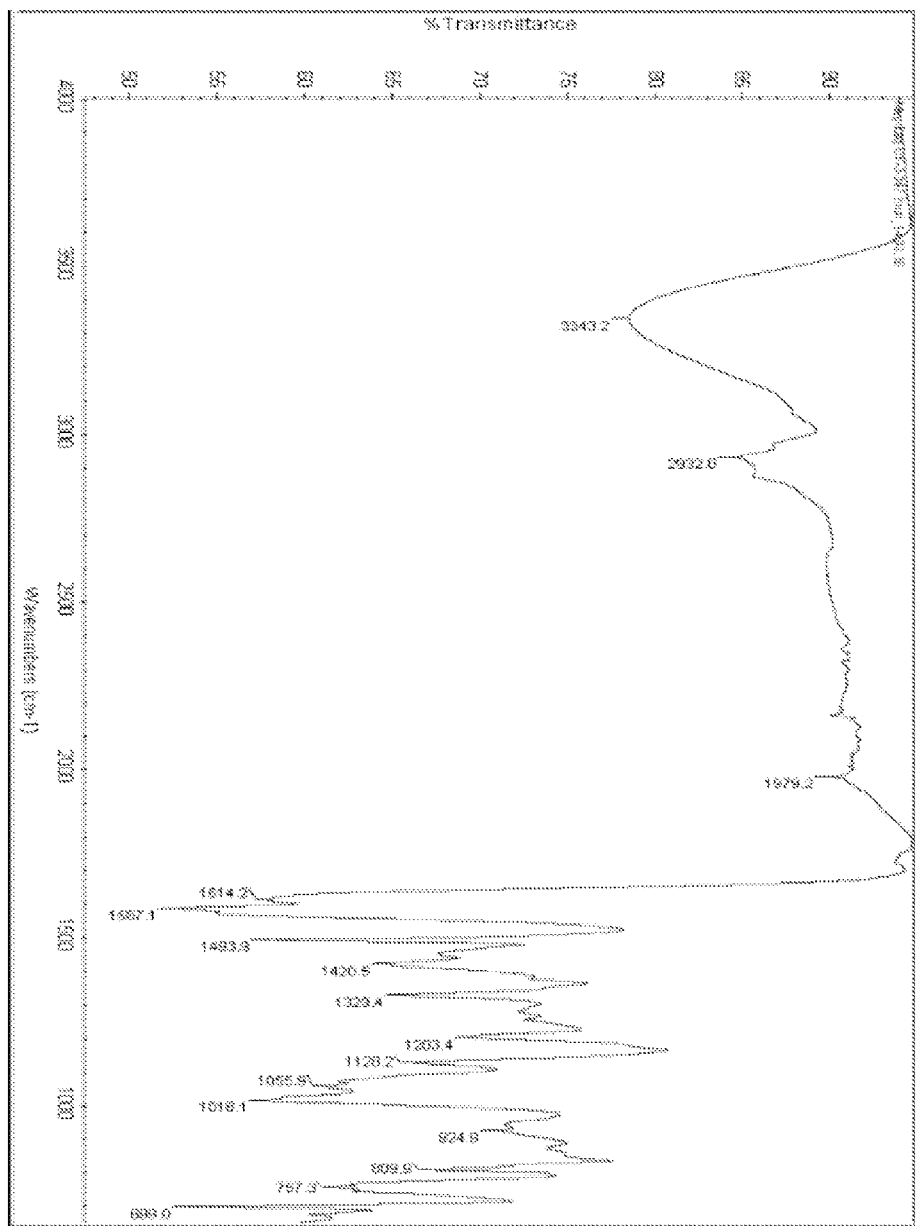
FIG. 8. FT-IR Spectrum of MEG-LAQ according to Example 1A.

The attenuated total reflectance (ATR) FT-IR spectrum of MEG-LAQ was measured with a Nicolet 6700 "Thermo Scientific" FT-IR apparatus. FIG. 8 shows a typical spectrum. A summary of the band assignments is shown in Table 3.

TABLE 3

Summary of IR Band Assignments of MEG-LAQ

| Transition Energy (cm$^{-1}$) | Band Assignment |
| --- | --- |
| 699-1239 | Aromatic C—H deformation vibration |
| 1016-1420 | C—N stretching |
| 1128-1203 | Aromatic C—OH stretching |
| 1587-1614 | Aromatic C—C stretching, Aromatic C=C stretching |
| 1614 | C=O stretching |
| 3343 | OH stretching |

Discussion:

MEG-LAQ may form under certain conditions when meglumine is used in LAQ formulation. For example, MEG-LAQ is formed at 40° C. and 75% Relative Humidity (accelerated conditions). MEG-LAQ is also formed at room temperature at <0.1%.

Example 1B

Formation of MEG-LAQ

MEG-LAQ was obtained from the reaction below:

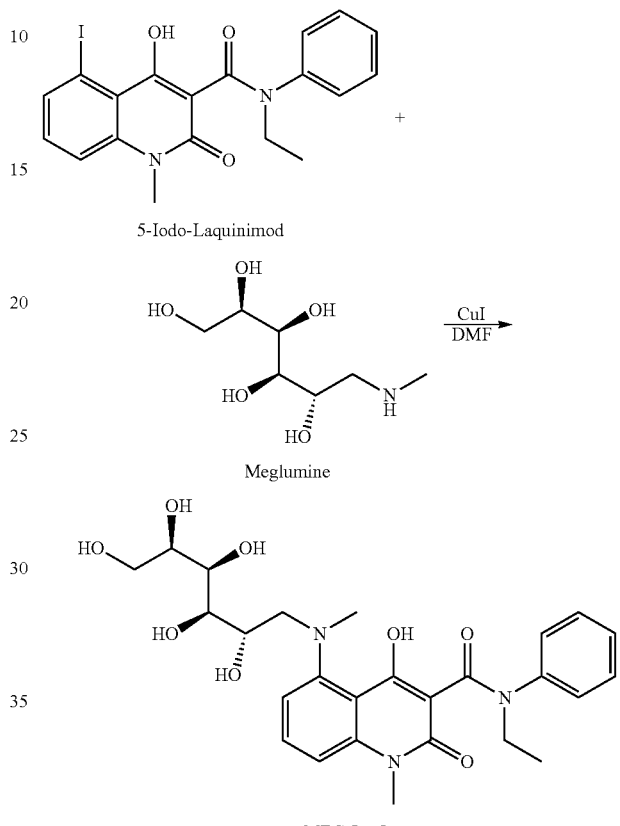

5-iodo-laquinimod, a new chemical entity, was prepared from 2-amino-6-iodobenzoic acid in a similar way that laquinimod was prepared from 2-amino-6-chlorobenzoic acid. (see, e.g., U.S. Pat. No. 6,077,851 and Wennerberg et al., Organic Process Research & Development (2007), 11(4): 674-680, the entire content of each of which is hereby incorporated by reference) The preparation of 5-iodo-laquinimod is shown below:

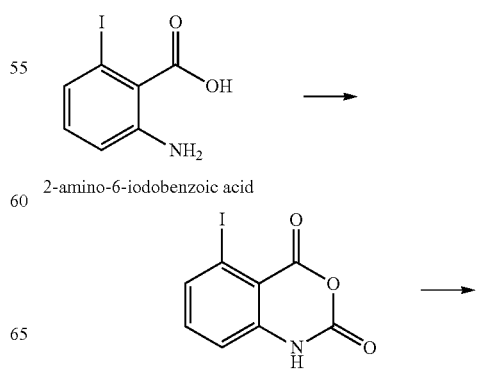

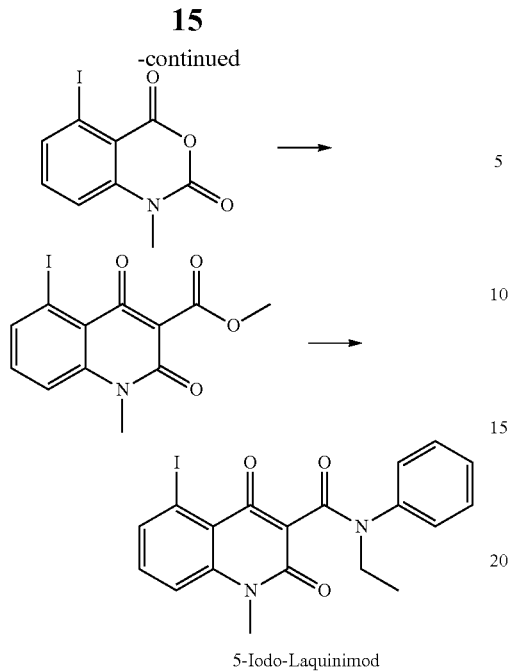

5-Iodo-Laquinimod 5-iodo-laquinimod (2.0 g, 4.46 mmol), meglumine (3 eq, 2.6 g, 13.4 mmol) and CuI (0.4 g, 1.9 mmol) were dissolved in dimethylformamide (DMF, 18 ml) at 35-38° C. under inert atmosphere. The reaction mixture was stirred for 2 hours at 35-38° C. followed by DMF distillation at 2 mbar vacuum. The green oily residue was dissolved in 100 ml methanol and silica gel (15 g, 0.06-0.2 mm) was added. The suspension was evaporated to dryness. Pure product was obtained by flash column chromatography on silica gel (0.04-0.06 mm). Mobile phase—15% methanol in dichloromethane. Yield: 0.88 g (38%).

MEG-LAQ may be formed in large excess of meglumine, accelerated conditions and aqueous media as described in Example 1A. However, the substitution of the chloride atom by the secondary amine of meglumine is not favorable and therefore this chemical transition is slow (approximately 1 month) and the resulting MEG-LAQ can be accompanied by other degradation products of laquinimod. As a result, tedious purifications are needed in order to isolate MEG-LAQ from the reaction mixture.

In comparison, the synthesis of MEG-LAQ according to Example 1B is straight forward. Although this aromatic chloride nucleophilic substitution is uncommon, the use of catalytic amount of CuI facilitates a fast reaction under moderate conditions. Therefore the method of Example 1B is advantageous over Example 1A.

Example 2

Manufacture of Formulations Comprising Laquinimod Sodium

Laquinimod capsules are manufactured according to the method as described in Example 2 of PCT International Application Publication No. WO 2007/146248, the entire content of which is hereby incorporated by reference. Steps of Example 2 of WO 2007/146248 are performed.

The quantity of MEG-LAQ in the capsules prepared are below the detection limit by HPLC or not more than 1.0% by weight relative to the amount of laquinimod.

Discussion:

Example 2 demonstrates that, in a commercial-scale production, pharmaceutical composition of laquinimod can be prepared with non-detectable level or a low level of MEG-LAQ (not more than 1.0% by weight).

What is claimed is:

1. A compound or an isolated compound having the structure:

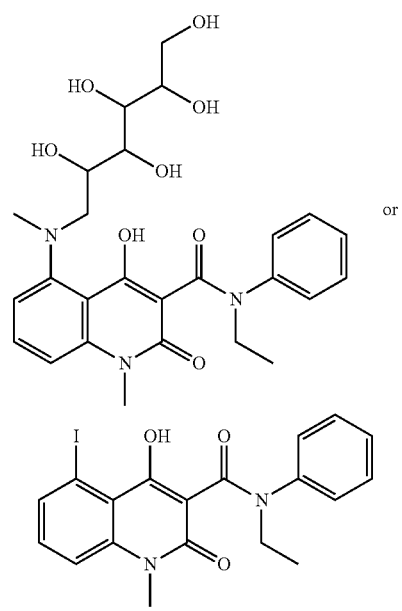

or a salt thereof.

2. The isolated compound of claim 1, in mono-hydrate form.

3. A composition comprising the compound of claim 1, said compound having the structure:

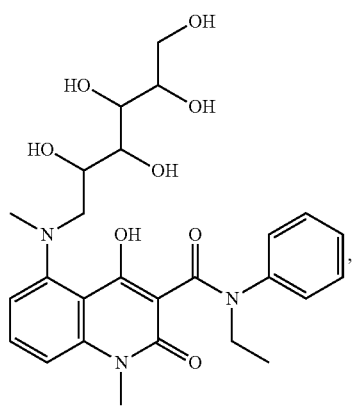 [SMILES: CCN(C(=O)c1c(O)c2c(N(C)CC(O)C(O)C(O)C(O)CO)cccc2n(C)c1=O)c1ccccc1]

or a salt thereof,
wherein the composition is free of laquinimod or a salt thereof.

4. The composition of claim 3, wherein the compound is in mono-hydrate form.

5. A process for preparing the compound of claim 1, said compound being N-ethyl-4-hydroxyl-1-methyl-5-(methyl(2,3,4,5,6-pentahydroxyhexyl)amino)-2-oxo-N-phenyl-1,2-dihydroquinoline-3-carboxamide, comprising the steps of:

a) reacting laquinimod or a salt thereof with meglumine in an aqueous solution;
b) adjusting the pH of the aqueous solution to less than 2; and
c) isolating and obtaining N-ethyl-4-hydroxyl-1-methyl-5-(methyl(2,3,4,5,6-pentahydroxyhexyl)amino)-2-oxo-N-phenyl-1,2-dihydroquinoline-3-carboxamide from the reaction mixture.

6. The process of claim 5, wherein the salt of laquinimod is a sodium salt.

7. A process for preparing the compound of claim 1, said compound being N-ethyl-4-hydroxyl-1-methyl-5-(methyl(2,3,4,5,6-pentahydroxyhexyl)amino)-2-oxo-N-phenyl-1,2-dihydroquinoline-3-carboxamide, comprising the steps of:
a) dissolving 5-iodo-laquinimod, meglumine and CuI in Dimethylformamide (DMF) to form a mixture;
b) removing DMF from the mixture of step a) to obtain an residue;
c) dissolving the residue of step b) in methanol to obtain a mixture;
d) adding silica gel to the mixture of step c) to obtain a suspension;
e) evaporating the suspension of step d) to dryness; and isolating and obtaining N-ethyl-4-hydroxyl-1-methyl-5-(methyl(2,3,4,5,6-pentahydroxyhexyl)amino)-2-oxo-N-phenyl-1,2-dihydroquinoline-3-carboxamide from the suspension of step e).

8. The process of claim 7,
a) wherein the mixture of step a) is stirred for 2 hours at 35-38° C. prior to step b), and/or
b) wherein step b) is achieved by DMF distillation at 2 mbar vacuum, and/or
c) wherein step f) achieved by flash column chromatography on silica gel.

9. N-ethyl-4-hydroxyl-1-methyl-5-(methyl(2,3,4,5,6-pentahydroxyhexyl)amino)-2-oxo-N-phenyl-1,2-dihydroquinoline-3-carboxamide prepared by the process of claim 5.

10. A pharmaceutical composition comprising laquinimod or a pharmaceutically acceptable salt thereof, the compound of claim 1, and at least one pharmaceutically acceptable carrier,
wherein the compound of claim 1 is N-ethyl-4-hydroxyl-1-methyl-5-(methyl(2,3,4,5,6-pentahydroxyhexyl)amino)-2-oxo-N-phenyl-1,2-dihydroquinoline-3-carboxamide and is present in the pharmaceutical composition in an amount greater than about 0.1% w/w, or greater than about 0.2% w/w relative to the amount of laquinimod, based on a determination by an HPLC method.

11. The pharmaceutical composition of claim 10, wherein N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount not more than about 1.0%, by weight, relative to the amount of laquinimod, based on a determination by an HPLC method.

12. The pharmaceutical composition of of claim 10, wherein the pharmaceutical composition is less than one week old, and the temperature during the less than one week did not exceed ambient temperature.

13. The pharmaceutical composition of claim 10, wherein the at least one pharmaceutically acceptable carrier is magnesium stearate.

14. The pharmaceutical composition of claim 10, comprising the pharmaceutically acceptable salt of laquinimod which is a sodium salt.

15. The pharmaceutical composition of claim 10, in the form of a capsule or a tablet.

16. A process for preparing a validated pharmaceutical composition or a packaged pharmaceutical composition, said pharmaceutical composition comprising laquinimod or a pharmaceutically acceptable salt thereof, and at least one pharmaceutically acceptable carrier, comprising:
a) obtaining a batch of laquinimod or a pharmaceutically acceptable salt thereof or a pharmaceutical composition of laquinimod or a pharmaceutically acceptable salt thereof;
b) determining the amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the batch using a suitable apparatus or analyzing the pharmaceutical composition for the presence of N-ethyl-4-hydroxyl-1-methyl-5-(methyl(2,3,4,5,6-pentahydroxyhexyl)amino)-2-oxo-N-phenyl-1,2-dihydroquinoline-3-carboxamide; and
c) preparing the pharmaceutical composition from the batch only if the batch is determined to have not more than about 1.0% N-ethyl-4-hydroxyl-1-methyl-5-(methyl(2,3,4,5,6-pentahydroxyhexyl)amino)-2-oxo-N-phenyl-1,2-dihydroquinoline-3-carboxamide by weight relative to the amount of laquinimod or packaging the pharmaceutical composition in a light-resistant packaging only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide is not more than about 1.0% by weight relative to the amount of laquinimod.

17. A process of preparing a pharmaceutical composition, or distributing a validated batch of a pharmaceutical composition, or preparing a packaged pharmaceutical composition, said pharmaceutical composition comprising laquinimod or a pharmaceutically acceptable salt thereof and at least one pharmaceutically acceptable carrier, comprising:
a) obtaining a batch of laquinimod or a pharmaceutically acceptable salt thereof or a batch of the pharmaceutical composition comprising laquinimod or a pharmaceutically acceptable salt thereof;
b) performing stability testing with a sample of the batch;
c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample by a suitable apparatus after stability testing; and
d) preparing the pharmaceutical composition from the batch or validating the batch for distribution or packaging the pharmaceutical composition only if the sample is determined to have not more than about 1.0% by weight of N-ethyl-4-hydroxyl-1-methyl-5-(methyl(2,3,4,5,6-pentahydroxyhexyl)amino)-2-oxo-N-phenyl-1,2-dihydroquinoline-3-carboxamide relative to the amount of laquinimod; and
e) optionally distributing the validated batch.

18. The process of claim 16, wherein the pharmaceutical composition comprises the pharmaceutically acceptable salt of laquinimod which is a sodium salt.

19. The compound of claim 1 for use, as a reference standard to detect trace amounts of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in a pharmaceutical composition comprising laquinimod or a pharmaceutically acceptable salt of laquinimod, wherein said compound of claim 1 is N-ethyl-4-hydroxyl-1-methyl-5-

(methyl(2,3,4,5,6-pentahydroxyhexyl)amino)-2-oxo-N-phenyl-2-dihydroquinoline-3-carboxamide.

20. A method for treating a patient afflicted with multiple sclerosis comprising administering to the patient an amount of the pharmaceutical composition of claim 10 effective to treat Multiple Sclerosis in the patient.

21. The compound of claim 1, wherein said compound is isolated N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof.

22. The isolated compound of claim 2, wherein said compound is isolated N-ethyl-4-hydroxyl-1-methyl-5-(methyl(2,3,4,5,6-pentahydroxyhexyl)amino)-2-oxo-N-phenyl-1,2-dihydroquinoline-3-carboxamide or a salt thereof.

23. The process of claim 8, wherein the mixture of step a) is stirred for 2 hours at 35-38° C. prior to step b).

24. The process of claim 8, wherein step b) is achieved by DMF distillation at 2 mbar vacuum.

25. The process of claim 8, wherein step f) is achieved by flash column chromatography on silica gel.

26. N-ethyl-4-hydroxyl-1-methyl-5-(methyl(2,3,4,5,6-pentahydroxyhexyl)amino)-2-oxo-N-phenyl-1,2-dihydroquinoline-3-carboxamide prepared by the process of claim 7.

27. The pharmaceutical composition of claim 10, wherein N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount greater than about 0.1% w/w relative to the amount of laquinimod, based on a determination by an HPLC method.

28. The pharmaceutical composition of claim 10, wherein N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount greater than about 0.2% w/w relative to the amount of laquinimod, based on a determination by an HPLC method.

29. The pharmaceutical composition of claim 27, wherein N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount not more than about 1.0%, by weight, relative to the amount of laquinimod, based on a determination by an HPLC method.

30. The pharmaceutical composition of claim 28, wherein N-ethyl-4-hydroxyl-1-methyl-5-(methyl(2,3,4,5,6-pentahydroxyhexyl)amino)-2-oxo-N-phenyl-1,2-dihydroquinoline-3-carboxamide is present in the pharmaceutical composition in an amount not more than about 1.0%, by weight, relative to the amount of laquinimod, based on a determination by an HPLC method.

31. The process of claim 16, comprising:
a) obtaining a batch of laquinimod or a pharmaceutically acceptable salt thereof;
b) determining the amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the batch using a suitable apparatus; and
c) preparing the pharmaceutical composition from the batch only if the batch is determined to have not more than about 1.0% N-ethyl-4-hydroxyl-1-methyl-5-(methyl(2,3,4,5,6-pentahydroxyhexyl)amino)-2-oxo-N-phenyl-1,2-dihydroquinoline-3-carboxamide by weight relative to the amount of laquinimod.

32. The process of claim 16, comprising:
a) obtaining a pharmaceutical composition of laquinimod or a pharmaceutically acceptable salt thereof;
b) analyzing the pharmaceutical composition for the presence of N-ethyl-4-hydroxyl-1-methyl-5-(methyl(2,3,4,5,6-pentahydroxyhexyl)amino)-2-oxo-N-phenyl-1,2-dihydroquinoline-3-carboxamide; and
c) packaging the pharmaceutical composition in a light-resistant packaging only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide is not more than about 1.0% by weight relative to the amount of laquinimod.

33. The process of claim 17, comprising:
a) obtaining a batch of the pharmaceutical composition;
b) performing stability testing with a sample of the batch;
c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample of the batch by a suitable apparatus after stability testing;
d) validating the batch for distribution only if the sample of the batch after stability testing is determined to have not more than about 1.0% by weight of N-ethyl-4-hydroxyl-1-methyl-5-(methyl(2,3,4,5,6-pentahydroxyhexyl)amino)-2-oxo-N-phenyl-1,2-dihydroquinoline-3-carboxamide relative to the amount of laquinimod; and
e) distributing the validated batch.

34. The process of claim 17, comprising:
a) obtaining a batch of laquinimod or a pharmaceutically acceptable salt thereof;
b) performing stability testing with a sample from the batch;
c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample by a suitable apparatus after stability testing; and
d) preparing the pharmaceutical composition from the batch only if the batch is determined to have not more than about 1.0% N-ethyl-4-hydroxyl-1-methyl-5-methyl(2,3,4,5,6-pentahydroxyhexyl)amino)-2-oxo-N-phenyl-1,2-dihydroquinoline-3-carboxamide by weight relative to the amount of laquinimod.

35. The process of claim 17, comprising:
a) obtaining a batch of pharmaceutical composition comprising laquinimod or a pharmaceutically acceptable salt thereof;
b) performing stability testing with a sample from the batch;
c) determining the total amount of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample by a suitable apparatus after stability testing; and
d) packaging the pharmaceutical composition In only if the content of N-ethyl-4-hydroxyl-1-methyl-5-(methyl(2,3,4,5,6-pentahydroxyhexyl)amino)-2-oxo-N-phenyl-1,2-dihydroquinoline-3-carboxamide in the sample is determined to be not more than about 1.0% by weight relative to the amount of laquinimod.

36. The process of claim 17, wherein the pharmaceutical composition comprises the pharmaceutically acceptable salt of laquinimod which is a sodium salt.

* * * * *